(12) United States Patent
Abdel-Magid et al.

(10) Patent No.: US 7,709,682 B2
(45) Date of Patent: May 4, 2010

(54) LYSINE SALTS OF 4-((PHENOXYALKYL)THIO)-PHENOXYACETIC ACID DERIVATIVES

(75) Inventors: Ahmed F. Abdel-Magid, Ambler, PA (US); Steven J. Mehrman, Quakertown, PA (US); Armin Roessier, Tengen (DE)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 11/531,464

(22) Filed: Sep. 13, 2006

(65) Prior Publication Data

US 2007/0060649 A1 Mar. 15, 2007

Related U.S. Application Data

(60) Provisional application No. 60/717,137, filed on Sep. 14, 2005.

(51) Int. Cl.
C07C 323/13 (2006.01)

(52) U.S. Cl. ...................................... 562/426

(58) Field of Classification Search ............... None
See application file for complete search history.

(56) References Cited

U.S. PATENT DOCUMENTS

| 4,513,006 | A | 4/1985 | Maryanoff et al. |
| 4,820,867 | A | 4/1989 | Belanger et al. |
| 5,360,909 | A | * 11/1994 | Igarashi et al. ............. 546/172 |
| 2004/0143006 | A1 | 7/2004 | Jeppesen et al. |
| 2005/0124698 | A1 | 6/2005 | Kuo et al. |
| 2006/0058382 | A1 | 3/2006 | Kuo et al. |
| 2006/0058393 | A1 | 3/2006 | DeAngelis et al. |
| 2006/0257987 | A1 | 11/2006 | Valcarcel et al. |

FOREIGN PATENT DOCUMENTS

| WO | WO 03/011807 | 2/2003 |
| WO | WO 03/074495 | 9/2003 |
| WO | WO 2005/030694 | 4/2005 |

OTHER PUBLICATIONS

Leibowitz, M. D., et al., "Activation of PPARδ alters lipid metabolism in db/db mice." *FEBS Letters*, 2000, pp. 333-336, vol. 473, No. 3.
Oliver, W. R., "A selective peroxisome proliferator-activated receptor δ agonist promotes reverse cholesterol transport." *PNAS*, 2001, pp. 5306-5311. vol. 98, No. 9.
Auboeuf et al., 1997, Diabetes 46(8):1319-1327.
Braissant et al., 1996, Endocrinology 137(1): 354-366.
Barak et al, 2002, Proc. Natl. Acad. Sci. USA 99(1):303-308.
Lawn et al., 1999, J. Clin. Investigation 104(8): R25-R31.
Tanaka et al, 2003, Proc. Natl. Acad. Sci. USA 100(26):15924-15929.
Wang et al., 2003, Cell 113:159-170.

* cited by examiner

*Primary Examiner*—Paul A Zucker

(57) ABSTRACT

The present invention is directed to a novel lysine salts, pharmaceutical compositions containing them and their use in the treatment of disorders and conditions modulated by PPAR delta. The present invention is further directed to a novel process for the preparation of said lysine salts.

4 Claims, 3 Drawing Sheets

XRD pattern for the non-hydrate, L-lysine salt of the compound of formula (Ia)

XRD pattern for the di-hydrate, L-lysine salt of the compound of formula (Ia)

Isotherm Plot, Beginning with the Non-Hydrate, L-lysine salt of the compound of formula (Ia) and Cycling 0-90% RH

LYSINE SALTS OF 4-((PHENOXYALKYL)THIO)-PHENOXYACETIC ACID DERIVATIVES

CROSS REFERENCE TO RELATED APPLICATIONS

This application claims the benefit of U.S. Provisional Application 60/717,137, filed on Sep. 14, 2005, which is incorporated by reference herein in its entirety.

FIELD OF THE INVENTION

The present invention is directed to novel lysine salts, pharmaceutical compositions containing them and their use in the treatment of disorders and conditions modulated by PPAR delta. More particularly, the compounds of the present invention are useful as lipid-lowering agents, blood-pressure lowering agents, or both. Additionally, the compounds are useful in treating, preventing, or inhibiting the progression of a condition directly or indirectly mediated by PPAR delta. Said condition includes, but is not limited to, diabetes, cardiovascular diseases, Metabolic X Syndrome, hypercholesterolemia, hypo-HDL-cholesterolemia, hyper-LDL-cholesterolemia, dyslipidemia, atherosclerosis, and obesity. The present invention is further directed to a novel process for the preparation of said lysine salts.

BACKGROUND OF THE INVENTION

U.S. Provisional Application No. 60/504,146, filed Sep. 19, 2003 and U.S. Non-provisional application Ser. No. 10/942,478 filed Sep. 16, 2004, which are herein incorporate by reference in their entirety, disclose compounds of formula (I) and pharmaceutically acceptable salts thereof, useful for treating, preventing and/or inhibiting the progression of a condition directly or indirectly mediated by PPAR delta. U.S. Provisional Application No. 60/504,146, filed Sep. 19, 2003 and U.S. Non-provisional application Ser. No. 10/942,478 filed Sep. 16, 2004 however, do not disclose crystalline salts of the compounds of formula (I), nor lysine salts of the compounds of formula (I).

SUMMARY OF THE INVENTION

The present invention is directed to a lysine salt of a compound of formula (I)

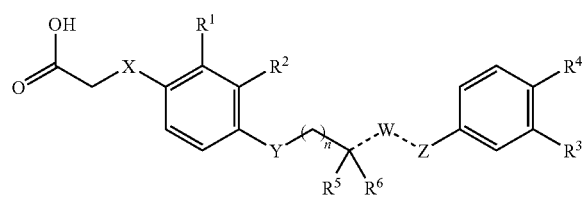

(I)

wherein
X is selected from a covalent bond, S, or O;
Y is S or O;
—W— represents a group selected from =CH—, —CH=, —CH$_2$—, —CH$_2$—, —CH$_2$—, =CH—CH$_2$—, —CH$_2$—CH=, =CH—CH=, and —CH=CH—;
Z is selected from O, CH, and CH$_2$; provided that when Y is O, then Z is O;

n is 1 or 2;
$R_1$ and $R_2$ are each independently selected from H, $C_{1-3}$alkyl, $C_{1-3}$alkoxy, halo, and $NR_aR_b$; wherein $R_a$ and $R_b$ are each independently H or $C_{1-3}$alkyl;
$R_3$ and $R_4$ are each independently selected from H, halo, cyano, hydroxy, acetyl, $C_{1-5}$alkyl, $C_{1-4}$alkoxy, and $NR_cR_d$; wherein $R_c$ and $R_d$ are each independently H or $C_{1-3}$alkyl; provided that $R_3$ and $R_4$ are not both H;
$R_5$ is selected from halo, phenyl, phenoxy, (phenyl)$C_{1-5}$alkoxy, (phenyl)$C_{1-5}$alkyl, $C_{2-5}$heteroaryloxy, $C_{2-5}$heteroaryl$C_{1-5}$alkoxy, $C_{2-5}$heterocyclyloxy, $C_{1-9}$alkyl, $C_{1-8}$alkoxy, $C_{2-9}$alkenyl, $C_{2-9}$alkenyloxy, $C_{2-9}$alkynyl, $C_{2-9}$alkynyloxy, $C_{3-7}$cycloalkyl, $C_{3-7}$cycloalkoxy, $C_{3-7}$cycloalkyl-$C_{1-7}$alkyl, $C_{3-7}$cycloalkyl-$C_{1-7}$alkoxy, $C_{3-7}$cycloalkyloxy-$C_{1-6}$alkyl, $C_{1-6}$alkoxy-$C_{1-6}$alkyl, $C_{1-5}$alkoxy-$C_{1-5}$alkoxy, or $C_{3-7}$cycloalkyloxy-$C_{1-7}$alkoxy;
and $R_6$ is H when —W— represents a group selected from —CH=, —CH$_2$—, —CH$_2$—CH$_2$—, —CH$_2$—CH=, and —CH=CH—;
or $R_6$ is absent when —W— represents a group selected from =CH—, =CH—CH$_2$—, and =CH—CH=.

In an embodiment of the present invention, the lysine salt of the compound of formula (I) is crystalline. In another embodiment, the present invention is directed to an L-lysine salt of the compound of formula (I). In another embodiment, the present invention is directed to a D-lysine salt of the compound of formula (I).

In an embodiment, the present invention is directed to a lysine salt of the compound of formula (Ia)

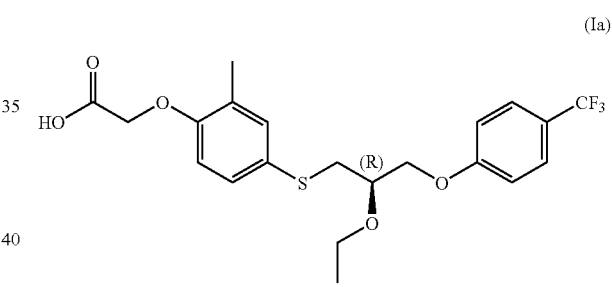

(Ia)

wherein the compound of formula (Ia) is also known as (R)-{4-[2-Ethoxy-3-(4-trifluoromethyl-phenoxy)-propylsulfanyl]-2-methyl-phenoxy}-acetic acid. The compound of formula (Ia) is a compound of formula (I) wherein X is O; Y is S; n is 1; —W— is —CH$_2$—; Z is O; $R_1$ is methyl; $R^2$ is hydrogen; $R^3$ is hydrogen; $R^4$ is trifluoromethyl; $R^5$ is (R)-ethoxy and $R^6$ is hydrogen.

In an embodiment of the present invention, the lysine salt of the compound of formula (Ia) is crystalline. In another embodiment, the present invention is directed to an L-lysine salt of the compound of formula (Ia). In another embodiment, the present invention is directed to a D-lysine salt of the compound of formula (Ia). In another embodiment, the present invention is directed to a non-hydrate, L-lysine salt of the compound of formula (Ia). In a preferred embodiment, the present invention is directed to a di-hydrate, L-lysine salt of the compound of formula (Ia).

The present invention is further directed to a process for the preparation of a lysine salt of the compound of formula (I), comprising reacting a compound of formula (I) with lysine, in a mixture comprising an organic solvent and water (preferably, in a mixture comprising $C_{1-4}$alcohol and water), to yield the corresponding lysine salt. In an embodiment, the present invention is directed to a process for the preparation of a lysine salt (preferably a crystalline, L-lysine salt, more preferably a crystalline, di-hydrate, L-lysine salt) of the compound of formula (Ia), comprising reacting the compound of formula (Ia) with lysine, in a mixture of one or more organic solvents and water (preferably, in a mixture comprising $C_{1-4}$alcohol and water). In a preferred embodiment, the present invention is directed to a process for the preparation of a lysine salt (preferably a crystalline, L-lysine salt, more preferably a crystalline, di-hydrate, L-lysine salt) of the compound of formula (Ia), comprising reacting the compound of formula (Ia) with lysine in a mixture of $C_{1-4}$alcohol, water and ethyl acetate, more preferably, in a mixture of methanol, water and ethyl acetate, to yield the corresponding lysine salt, In a preferred embodiment, the present invention is directed to a process for the preparation of a lysine salt (preferably a crystalline, L-lysine salt, more preferably a crystalline, di-hydrate, L-lysine salt) of the compound of formula (Ia), comprising reacting the compound of formula (Ia) with lysine in a mixture of ethanol, isopropanol, methanol, and water, to yield the corresponding lysine salt.

The present invention is further directed to a product prepared according to any of the processes described herein.

Illustrative of the invention is a pharmaceutical composition comprising a pharmaceutically acceptable carrier and the product prepared according to any of the processes described herein. An illustration of the invention is a pharmaceutical composition made by mixing the product prepared according to any of the processes described herein and a pharmaceutically acceptable carrier. Illustrating the invention is a process for making a pharmaceutical composition comprising mixing the product prepared according to any of the processes described herein and a pharmaceutically acceptable carrier.

Exemplifying the invention are methods of treating a disorder mediated by the PPAR delta receptor, comprising administering to a subject in need thereof a therapeutically effective amount of any of the compounds or pharmaceutical compositions described above.

In an embodiment, the present invention is directed to methods for treating, preventing, or inhibiting the onset and/or progression of, a condition directly or indirectly mediated by PPAR delta. Said condition includes, but is not limited to, diabetes, cardiovascular diseases, Metabolic X Syndrome, hypercholesterolemia, hypo-HDL-cholesterolemia, hyper-LDL-cholesterolemia, dyslipidemia, atherosclerosis, and obesity.

Examples of conditions that can be treated with a PPAR delta-agonist include, without limitation, diabetes, cardiovascular diseases, Metabolic X Syndrome, hypercholesterolemia, hypo-HDL-cholesterolemia, hyper-LDL-cholesterolemia, dyslipidemia, atherosclerosis, and obesity. Dyslipidemia includes hypertriglyceridemia, and mixed hyperlipidemia. For example, dyslipidemia (including hyperlipidemia) may be one or more of the following conditions: low HDL (<35 or 40 mg/dl), high triglycerides (>200 mg/dl), and high LDL (>150 mg/dl).

Another example of the invention is the use of any of the compounds described herein in the preparation of a medicament for treating: (a) phase I hyperlipidemia, (b) pre-clinical hyperlipidemia, (c) phase II hyperlipidemia, (d) hypertension, (e) CAD (coronary artery disease), (f) coronary heart disease, (g) hypertriglyceridemia, (h) for lowering serum levels of low-density lipoproteins (LDL), (i) for lowering serum levels of intermediate density lipoprotein (IDL), (j) for lowering serum levels of small-density LDL, (k) for lowering fasting plasma glucose (FPG)/HbA1c, (l) for lowering blood pressure, (m) Type II diabetes, (n) Metabolic Syndrome X, (o) dyslipidemia, (p) artherosclerosis or (q) obesity, in a subject in need thereof.

DETAILED DESCRIPTION OF THE INVENTION

Figure 1:
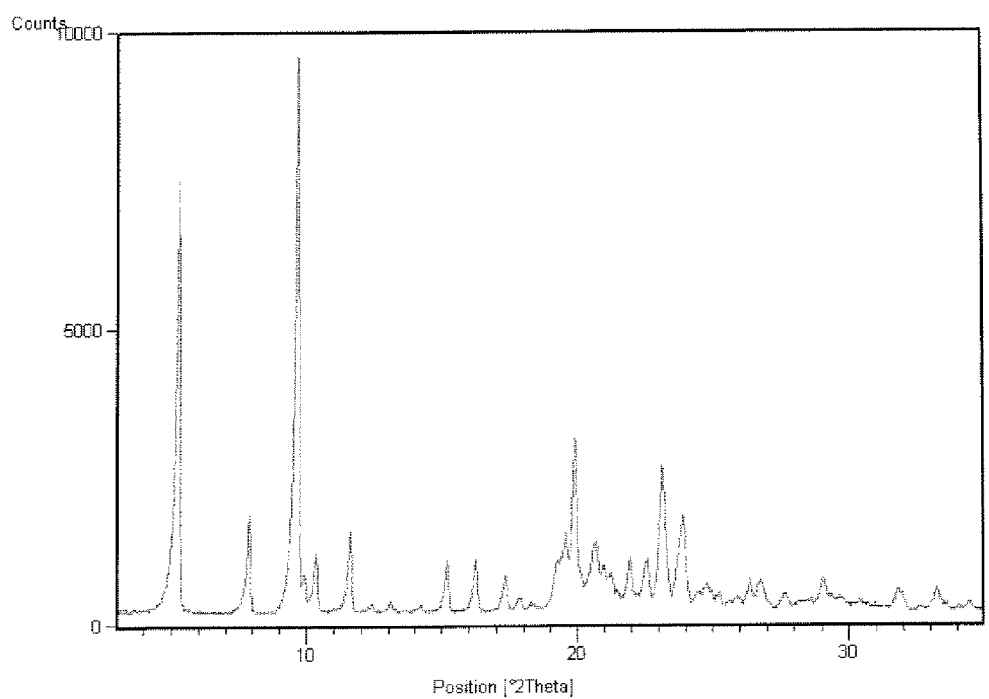
FIG. 1 Illustrates the XRD pattern for the non-hydrate, L-lysine salt of the compound of formula (Ia), measured as described herein.
Figure 2:
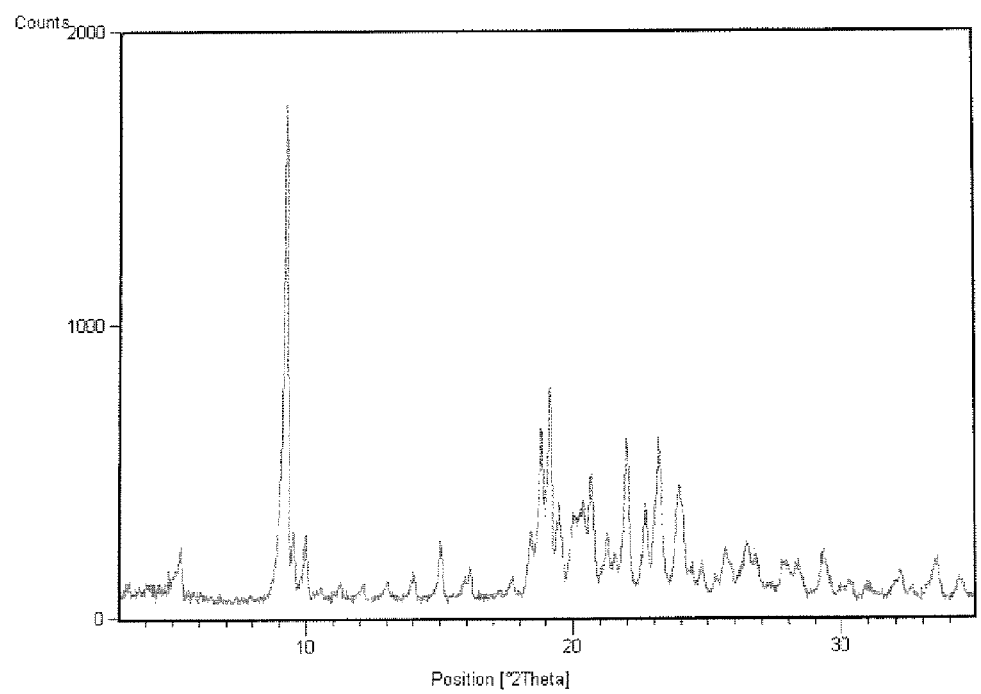
FIG. 2 Illustrates the XRD pattern for the di-hydrate, L-lysine salt of the compound of formula (Ia), measured as described herein.

The present invention is directed to a lysine salt of a compound of formula (I)

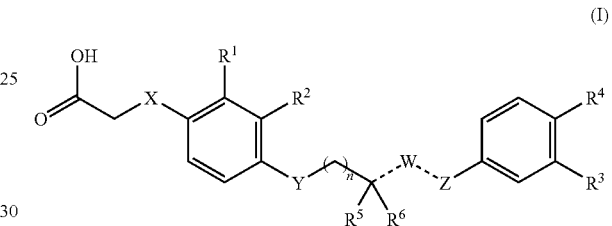

wherein X, Y, —W—, Z, n, $R^1$, $R^2$, $R^3$, $R^4$, $R^5$ and $R^6$ are as herein defined and processes for their preparation. The compounds of formula (I) are PPAR delta agonists, preferably selective PPAR delta agonists The salts of the present invention are useful as lipid-lowering agents, blood-pressure lowering agents, and/or agents useful for treating, preventing, or inhibiting the progression of, a condition directly or indirectly mediated by PPAR delta, including, but is not limited to, diabetes, cardiovascular diseases, Metabolic X Syndrome, hypercholesterolemia, hypo-HDL-cholesterolemia, hyper-LDL-cholesterolemia, dyslipidemia, atherosclerosis, and obesity.

As used herein, conditions directly or indirectly "mediated by PPAR delta" include, but are not limited to, diabetes, cardiovascular diseases, Metabolic X Syndrome, hypercholesterolemia, hypo-HDL-cholesterolemia, hyper-LDL-cholesterolemia, dyslipidemia, atherosclerosis, and obesity.

As used herein, "dyslipidemia" includes hypertriglyceridemia, and mixed hyperlipidemia. For example, dyslipidemia (including hyperlipidemia) may be one or more of the following conditions: low HDL (<35 or 40 mg/dl), high triglycerides (>200 mg/dl), and high LDL (>150 mg/dl), The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation, prevention, treatment, or the delay of the onset or progression of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

For therapeutic purposes, the term "jointly effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term "Jointly effective amount" refers to that amount of each active compound or pharmaceutical agent, alone or in combination, that treats or inhibits in a subject the onset or progression of a disorder as being sought by a researcher, veterinarian, medical doctor or other clinician. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both (or more) drugs are administered in an amount that is sub-therapeutic or sub-prophylactic if administered alone, but are therapeutic or prophylactic when administered together.

The term "halogen" or "halo" shall include iodo, bromo, chloro and fluoro.

Unless otherwise noted, as used herein and whether used alone or as part of a substituent group, "alkyl" and "alkoxy" include straight and branched chains having 1 to 8 carbon atoms, such as $C_{1-6}$, $C_{1-4}$, $C_{3-8}$, $C_{2-5}$, or any other range, and unless otherwise noted, include both substituted and unsubstituted moieties. For example, $C_{1-6}$alkyl radicals include methyl, ethyl, n-propyl, isopropyl, n-butyl, isobutyl, sec-butyl, t-butyl, n-pentyl, 3-(2-methyl)butyl, 2-pentyl, 2-methylbutyl, neopentyl, n-hexyl, 2-hexyl and 2-methylpentyl. Alkoxy radicals are formed from the previously described straight or branched chain alkyl groups.

"Alkyl" and "alkoxy" include unsubstituted or substituted moieties with one or more substitutions, such as between 1 and 5, 1 and 3, or 2 and 4 substituents. The substituents may be the same (dihydroxy, dimethyl), similar (chloro, fluoro), or different (chlorobenzyl- or aminomethyl-substituted). Examples of substituted alkyl include haloalkyl (such as fluoromethyl, chloromethyl, difluoromethyl, perchloromethyl, 2-bromoethyl, trifluoromethyl, and 3-iodocyclopentyl), hydroxyalkyl (such as hydroxymethyl, hydroxyethyl, 2-hydroxypropyl), aminoalkyl (such as aminomethyl, 2-aminoethyl, 3-aminopropyl, and 2-aminopropyl), alkoxyalkyl, nitroalkyl, alkylalkyl, cyanoalkyl, phenylalkyl, heteroarylalkyl, heterocyclylalkyl, phenoxyalkyl, heteroaryloxyalkyl (such as 2-pyridyloxyalkyl), heterocyclyloxy-alkyl (such as 2-tetrahydropyranoxy-alkyl), thioalkylalkyl (such as MeS-alkyl), thiophenylalkyl (such as phS-alkyl), carboxylalkyl, and so on. A di($C_{1-3}$alkyl)amino group includes independently selected alkyl groups, to form, for example, methylpropylamino and isopropylmethylamino, in addition dialkylamino groups having two of the same alkyl group such as dimethyl amino or diethylamino.

The term "alkenyl" includes optionally substituted straight chain and branched hydrocarbon radicals as above with at least one carbon-carbon double bond ($sp^2$). Alkenyls include ethenyl (or vinyl), prop-1-enyl, prop-2-enyl (or allyl), isopropenyl (or 1-methylvinyl), but-1-enyl, but-2-enyl, butadienyls, pentenyls, hexa-2,4-dienyl, and so on. Hydrocarbon radicals having a mixture of double bonds and triple bonds, such as 2-penten-4-ynyl, are grouped as alkynyls herein. Alkenyl includes cycloalkenyl. Cis and trans or (E) and (Z) forms are included within the invention. "Alkenyl" may be substituted with one or more substitutions including, but not limited to, cyanoalkenyl, and thioalkenyl.

The term "alkynyl" includes optionally substituted straight chain and branched hydrocarbon radicals as above with at least one carbon-carbon triple bond (sp). Alkynyls include ethynyl, propynyls, butynyls, and pentynyls. Hydrocarbon radicals having a mixture of double bonds and triple bonds, such as 2-penten-4-ynyl, are grouped as alkynyls herein. Alkynyl does not include cycloalkynyl.

The term "Ac" as used herein, whether used alone or as part of a substituent group, means acetyl ($CH_3CO$—).

The terms "aryl" or "Ar" as used herein refer to an unsubstituted or substituted aromatic hydrocarbon ring system such as phenyl and naphthyl. When the Ar or aryl group is substituted, it may have one to three substituents which are independently selected from $C_1$-$C_8$alkyl, $C_1$-$C_8$alkoxy, fluorinated $C_1$-$C_8$alkyl (e.g., trifluoromethyl), fluorinated $C_1$-$C_8$alkoxy (e.g., trifluoromethoxy), halogen, cyano, $C_1$-$C_8$alkylcarbonyl such as acetyl, carboxyl, hydroxy, amino, nitro, $C_1$-$C_4$alkylamino (i.e., —NH—$C_1$-$C_4$alkyl), $C_1$-$C_4$ dialkylamino (i.e., —N—[$C_1$-$C_4$alkyl]$_2$ wherein the alkyl groups can be the same or different), or unsubstituted, mono-, di- or tri-substituted phenyl wherein the substituents on the phenyl are independently selected from $C_1$-$C_8$alkyl, $C_1$-$C_8$ alkoxy, fluorinated $C_1$-$C_8$ alkyl, fluorinated $C_1$-$C_8$ alkoxy, halogen, cyano, acetyl, carboxyl, hydroxy, amino, nitro, alkylamino, dialkylamino or five or six membered heteroaryl having 1-3 heteroatoms selected from N, O and S.

The term "heteroaryl" as used herein represents a stable, unsubsituted or substituted five or six membered monocyclic or bicyclic aromatic ring system which consists of carbon atoms and from one to three heteroatoms selected from N, O and S. The heteroaryl group may be attached at any heteroatom or carbon atom which results in the creation of a stable structure. Examples of heteroaryl groups include, but are not limited to, benzimidazolyl, benzisoxazolyl, benzofuranyl, benzopyrazolyl, benzothiadiazolyl, benzothiazolyl, benzothienyl, benzotriazolyl, benzoxazolyl, furanyl, furazanyl, furyl, imidazolyl, indazolyl, indolizinyl, indolinyl, indolyl, isobenzofuranyl, isoindolyl, isothiazolyl, isoxazolyl, oxazolyl, purinyl, pyrazinyl, pyrazolyl, pyridazinyl, pyridinyl, pyrimidinyl, pyrrolyl, quinolinyl, quinolyl, thiadiazolyl, thiazolyl, thiophenyl, or triazolyl. When the heteroaryl group is substituted, the heteroaryl group may have one to three substituents including, but not limited to, $C_1$-$C_8$alkyl, halogen, and aryl.

The term "heterocyclyl" includes optionally substituted nonaromatic rings having carbon atoms and at least one heteroatom (O, S, N) or heteroatom moiety ($SO_2$, CO, CONH, COO) in the ring. A heterocyclyl may be saturated, partially saturated, nonaromatic, or fused. Examples of heterocyclyl include cyclohexylimino, imdazolidinyl, imidazolinyl, morpholinyl, piperazinyl, piperidyl, pyridyl, pyranyl, pyrazolidinyl, pyrazolinyl, pyrrolidinyl, pyrrolinyl, and thienyl.

Unless otherwise indicated, heteroaryl and heterocyclyl may have a valence connecting it to the rest of the molecule through a carbon atom, such as 3-furyl or 2-imidazolyl, or through a heteroatom, such as N-piperidyl or 1-pyrazolyl. Preferably a monocyclic heterocyclyl has between 5 and 7 ring atoms, or between 5 and 6 ring atoms; there may be between 1 and 5 heteroatoms or heteroatom moieties in the ring, and preferably between 1 and 3, or between 1 and 2 heteroatoms or heteroatom moieties.

Heterocyclyl and heteroaryl also include fused, e.g., bicyclic, rings, such as those optionally fused with an optionally substituted carbocyclic or heterocyclic five- or six-membered aromatic ring. For example, "heteroaryl" includes an optionally substituted six-membered heteroaromatic ring containing 1, 2 or 3 nitrogen atoms fused with an optionally substituted five- or six-membered carbocyclic or heterocyclic aromatic ring. Said heterocyclic five- or six-membered aromatic ring fused with the said five- or six-membered aromatic ring may contain 1, 2 or 3 nitrogen atoms where it is a six-membered ring, or 1, 2 or 3 heteroatoms selected from oxygen, nitrogen and sulfur where it is a five-membered ring.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Where chemical moieties are combined, such as in ethoxymethyl or phenylethyl, the term is described in the direction from the periphery to the connection point of the rest of the molecule. For example, ethoxymethyl is $CH_3CH_2OCH_2$— and phenylethyl is a phenyl group linked by —$CH_2CH_2$— to the rest of the molecule (and not a phenyl group linked to the molecule with a $CH_3CH_2$ group as a substituent on the phenyl.) Where parentheses are used, they indicate a peripheral substitution.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

As used herein, unless otherwise noted, the term "aprotic solvent" shall mean any solvent that does not yield a proton. Suitable examples include, but are not limited to DMF, dioxane, THF, acetonitrile, pyridine, dichloroethane, dichloromethane, MTBE, toluene, and the like.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

As used herein, the abbreviation "KF" shall mean the weight percent of water in a product, as determined by the Karl-Fischer test.

The present invention is directed to lysine salts of the compound of formula (I), as herein defined. The lysine salts of the compound of formula (I) may be prepared by reacting a suitably substituted compound of formula (I) with lysine, preferably L-lysine or D-lysine, more preferably, L-lysine; in a mixture of an organic solvent such as methanol, ethanol, isopropanol, tetrahydrofuran (THF), methyl-t-butyl ethyl (MTBE), diethyl ether, combinations thereof, and the like; and water; preferably a mixture of $C_{1-4}$alcohol and water to yield the corresponding lysine salt of the compound of formula (I) Preferably, the compound of formula (I) is at least partially soluble in the mixture of organic solvent and water.

Preferably, the compound of formula (I), the lysine and the mixture of organic solvent and water are heated to dissolve the compound of formula (I); more preferably, the compound of formula (I), the lysine and the mixture of organic solvent and water are heated to reflux and then cooled to precipitate the corresponding lysine salt of the compound of formula (I).

Alternatively, the lysine salt of the compound of formula (I) may be isolated by evaporation of the reaction solvent—i.e. the mixture of organic solvent and water.

In an embodiment, the present invention is directed to a L-lysine salt of the compound of formula (Ia). In another embodiment, the L-lysine salt of the compound of formula (Ia) is a non-hydrate or di-hydrate.

The L-lysine salt of the compound of formula (Ia) may be prepared by reacting the compound of formula (Ia) with L-lysine; in a mixture of one or more organic solvents and water, preferably in a mixture comprising $C_{1-4}$alcohol and water, more preferably in a mixture comprising methanol and water; more preferably in a mixture comprising methanol and water in which the water is present in an amount greater than or equal to about 2 molar equivalents, more preferably, in a mixture comprising methanol and water wherein the water is present in an amount in the range of from about 2 to about 3 molar equivalents;

wherein the compound of formula (Ia), the L-lysine and the mixture comprising organic solvent(s) and water are heated to dissolve of the compound of formula (Ia), preferably, the compound of formula (Ia), the lysine and the mixture comprising organic solvent(s) and water are heated to reflux and then cooled to precipitate the corresponding L-lysine salt of the compound of formula (Ia), as a di-hydrate.

The L-lysine salt of the compound of formula (Ia) may be prepared by reacting the compound of formula (Ia) with L-lysine, in a mixture of one or more organic solvents and water, preferably in a mixture comprising $C_{1-4}$alcohol and water, more preferably in a mixture comprising methanol and water; more preferably in a mixture comprising methanol and water in which the water is present in an amount greater than or equal to about 2 molar equivalents, more preferably, in a mixture comprising methanol and water wherein the water is present in an amount in the range of from about 2 to about 3 molar equivalents;

more preferably in a mixture comprising ethanol, isopropanol, methanol, and water;

more preferably in a mixture comprising $C_{1-4}$alcohol, water and ethyl acetate, more preferably in a mixture of methanol, water and ethyl acetate, more preferably, in a mixture of methanol, water and ethyl acetate, wherein the ratio of methanol:water-ethyl acetate is in the range of from about 20:1:5 to about 20:1:30; more preferably, in a mixture of methanol, water and ethyl acetate, wherein the ratio of methanol water:ethyl acetate is about 20:1:20;

wherein the compound of formula (Ia), the L-lysine and the mixture comprising organic solvent(s) and water are heated to dissolve of the compound of formula (Ia), preferably, the compound of formula (Ia), the lysine and the mixture comprising organic solvent(s) and water are heated to reflux and then cooled to precipitate the corresponding L-lysine salt of the compound of formula (Ia), as a non-hydrate.

The non-hydrate L-lysine salt of the compound of formula (Ia) may be prepared from the corresponding di-hydrate L-lysine salt of the compound of formula (Ia) by drying the di-hydrate L-lysine salt of the compound of formula (Ia) under heat and/or vacuum, preferably under heat and vacuum to drive off the water. The di-hydrate L-lysine salt of the compound of formula (Ia) may be prepared from the corresponding non-hydrate L-lysine salt of the compound of formula (Ia) by subjecting the non-hydrate L-lysine salt of the compound of formula (Ia) to greater than or equal to about 30% RH (% relative humidity), preferably to between about 30% RH and about 80% RH.

In an embodiment, the L-lysine salt of the compound of formula (Ia) is crystalline. In another embodiment, the L-lysine salt of the compound of formula (Ia) is a non-hydrate or a di-hydrate, preferably, a di-hydrate, preferably, a di-hydrate as measured by Karl-Fischer. Preferably, the L-lysine salt of the compound of formula (Ia) is crystalline and di-hydrate.

The crystalline, di-hydrate L-lysine salt of the compound of formula (Ia) may be represented by the following chemical structure:

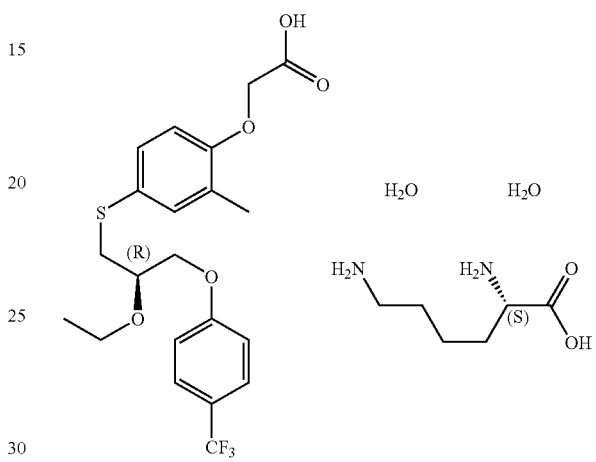

The crystalline, non-hydrate L-lysine salt of the compound of formula (Ia) may be represented by the following chemical structure:

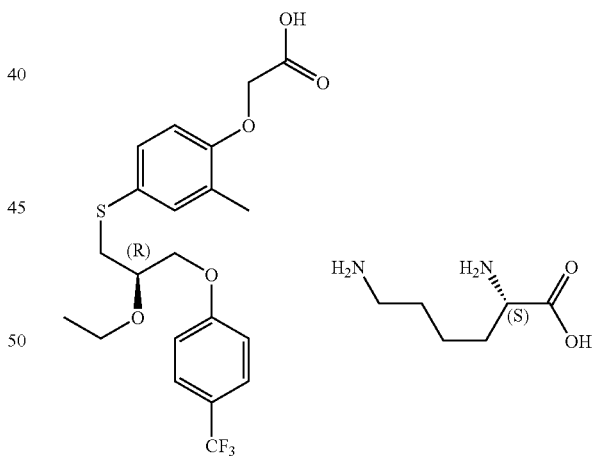

The X-ray diffraction patterns listed herein were measured using an X-Celerator detector. The sample was backloaded into a conventional x-ray holder. The sample was scanned from 3 to 35°2θ with a step size of 0.0165° 2 θ and a time per step of 10.16 seconds. The effective scan speed was 0.2067°/s. Instrument voltage and current settings were 45 kV and 40 mA.

The crystalline non-hydrate L-lysine salt of the compound of formula (Ia), may be characterized by its X-ray diffraction pattern, comprising the peaks as listed in Table 1, below.

TABLE 1

Non-hydrate, L-lysine Salt

| Position [°2θ] | d-spacing [Å] | Relative Intensity [%] |
|---|---|---|
| 5.270 | 16.7702 | 80.03 |
| 7.882 | 11.2170 | 17.44 |
| 9.683 | 9.1342 | 100.00 |
| 10.370 | 8.5312 | 10.61 |
| 11.611 | 7.6218 | 14.62 |
| 19.561 | 4.5383 | 15.03 |
| 19.921 | 4.4571 | 32.77 |
| 20.652 | 4.3009 | 13.83 |
| 21.963 | 4.0471 | 10.23 |
| 23.162 | 3.8403 | 27.02 |
| 23.710 | 3.7527 | 11.49 |
| 23.883 | 3.7228 | 17.86 |
| 23.969 | 3.7188 | 14.34 |

Preferably, the crystalline non-hydrate L-lysine salt of the compound of formula (Ia) is characterized by its XRD pattern which comprises peaks having a relative intensity greater than or equal to about 25%, as listed in Table 2 below.

TABLE 2

Non-hydrate, L-lysine Salt

| Position [°2θ] | d-spacing [Å] | Relative Intensity [%] |
|---|---|---|
| 5.270 | 16.7702 | 80.03 |
| 9.683 | 9.1342 | 100.00 |
| 19.921 | 4.4571 | 32.77 |
| 23.162 | 3.8403 | 27.02 |

The crystalline di-hydrate L-lysine salt of the compound of formula (Ia), may be characterized by its X-ray diffraction pattern, comprising the peaks as listed in Table 3 below.

TABLE 3

Di-hydrate, L-Lysine Salt

| Position [°2θ] | d-spacing [Å] | Relative Intensity [%] |
|---|---|---|
| 5.285 | 16.7225 | 11.63 |
| 9.255 | 9.5558 | 100.00 |
| 9.501 | 9.3085 | 14.59 |
| 9.976 | 8.8665 | 13.80 |
| 15.017 | 5.8997 | 12.10 |
| 18.417 | 4.8176 | 14.48 |
| 18.799 | 4.7205 | 35.27 |
| 19.102 | 4.6462 | 45.78 |
| 19.430 | 4.5686 | 19.02 |
| 19.990 | 4.4418 | 17.19 |
| 20.327 | 4.3689 | 19.12 |
| 20.643 | 4.3028 | 26.91 |
| 21.276 | 4.1762 | 13.07 |
| 21.989 | 4.0423 | 33.52 |
| 22.693 | 3.9185 | 17.96 |
| 23.187 | 3.8361 | 32.42 |
| 23.931 | 3.7186 | 24.24 |
| 24.084 | 3.6953 | 18.48 |
| 25.642 | 3.4741 | 10.03 |
| 26.462 | 3.3683 | 12.05 |
| 27.973 | 3.1897 | 11.23 |

Preferably, the crystalline di-hydrate L-lysine salt of the compound of formula (Ia) is characterized by its XRD pattern which comprises peaks having a relative intensity greater than or equal to about 25%, as listed in Table 4 below.

TABLE 4

Di-hydrate, L-Lysine Salt

| Position [°2θ] | d-spacing [Å] | Relative Intensity [%] |
|---|---|---|
| 9.255 | 9.5558 | 100.00 |
| 18.799 | 4.7205 | 35.27 |
| 19.102 | 4.6462 | 45.78 |
| 20.643 | 4.3028 | 26.91 |
| 21.989 | 4.0423 | 33.52 |
| 23.187 | 3.8361 | 32.42 |

In an embodiment, the L-lysine salt of the compound of formula (Ia) is characterized by the peak positions (in °2θ) in its XRD spectra for peaks with a relative intensity greater than about 10%, preferably with a relative intensity greater than about 25%.

Karl-Fischer values were measured for representative samples of the di-hydrate and non-hydrate L-lysine salts of the compound of formula (Ia) with results as listed below:

| Form | % KF |
|---|---|
| Non-hydrate (Batch N1) | 2.13% |
| Di-hydrate (Batch D1) | 5.4% |
| Di-hydrate (Batch D2) | 5.74% |

Figure 3:
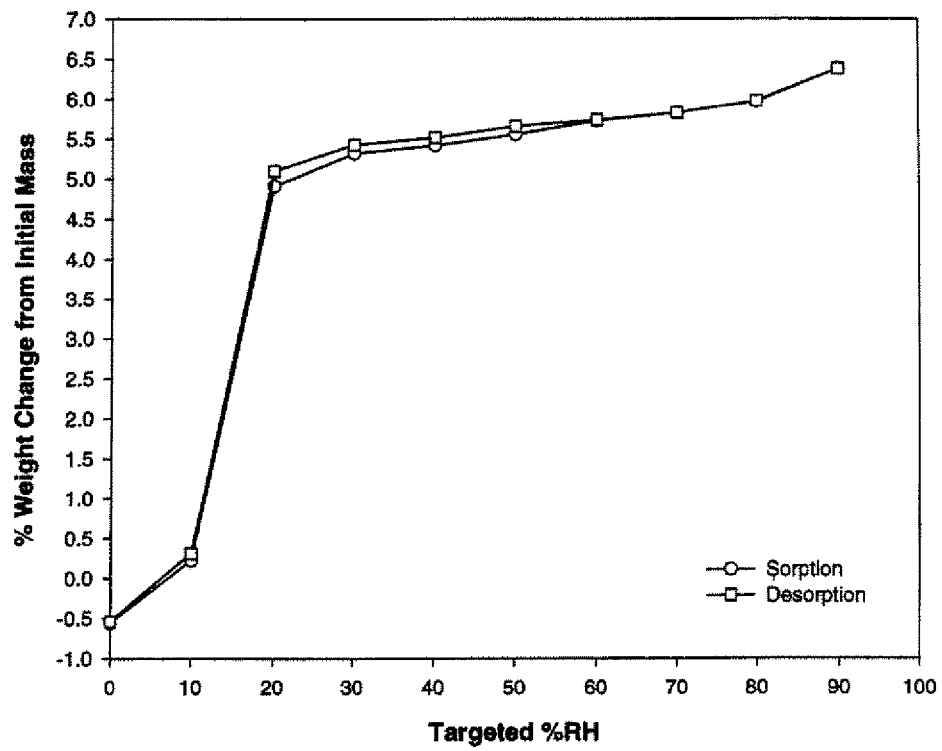
FIG. 3 Illustrates the DVS isotherm, cycling 0-90% RH, for the L-lysine salt of the compound of formula (Ia), measured as described herein.

The non-hydrate, L-lysine salt of the compound of formula (Ia) was subjected to cycling humidity conditions, with results as shown in FIG. 3. More specifically, the sample was analyzed through a full cycle in step mode at 25° C., from 0-90% RH (relative humidity) in 10% RH increments. The equilibration conditions set were as follows: dm/dt of 0.0007, dm/dt window of 5 mins; minimum and maximum stages of 15 and 360 minutes. Data was collected in 1 minute intervals. Nitrogen was used as the carrier gas.

The results from this experiment indicated that the non-hydrate, L-lysine salt of the compound of formula (Ia) reversibly converts to the corresponding di-hydrate form by absorbing water. The di-hydrate form was determined to be stable between about 30% RH and about 80% RH.

The solubility of representative samples of the compound of formula (Ia) and an L-lysine salt of the compound of formula (Ia) in distilled water was measured according to known methods, with results as listed in Table 5, below.

TABLE 5

| Solubility in Distilled Water | |
|---|---|
| Compound of formula (Ia) (free acid) | <0.002 mg/mL @ pH 2.0 |
|  | ~1.0 mg/mL @ pH 7.4 |
|  | $pK_a = 3.63$ |
| L-lysine salt of compound of formula (Ia) | 230 mg/mL @ pH 7.81 |

The salts of the present invention are PPAR delta agonists and are therefore useful in treating or inhibiting the progression of PPAR delta mediated conditions, such as diabetes, cardiovascular diseases, Metabolic X Syndrome, hypercholesterolemia, hypo-HDL-cholesterolemia, hyper-LDL-cholesterolemia, dyslipidemia, atherosclerosis, obesity, and complications thereof. For instance, complications of diabetes include such conditions as neuropathy, nephropathy, and retinopathy.

The present invention further comprises pharmaceutical compositions containing one or more of the lysine salts of the compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01-1000 mg, preferably from about 1-1000 mg, more preferably from about 10-500 mg and may be given at a dosage of from about 0.001-20.0 mg/kg/day, preferably from about 0.001-5.0 mg/kg/day, more preferably from about 0.01-0.5 mg/kg/day. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.01 to about 1000 mg of the active ingredient of the present invention The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating PPAR delta mediated disorders described in the present invention may also be carried out using a pharmaceutical composition comprising any of the compounds as defined herein and a pharmaceutically acceptable carrier. The pharmaceutical composition may contain between about 0.01 mg and 1000 mg, preferably about 0.1 to 500 mg, more preferably about 10 to 500 mg of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

Compounds of this invention may be administered in any of the foregoing compositions and according to dosage regimens established in the art whenever treatment of disorders mediated by PPAR delta is required.

The daily dosage of the products may be varied over a wide range from 0.01 to 1,000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.001 mg/kg to about 5 mg/kg of body weight per day, preferably, the range is from about 0.01 to about 0.5 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The salts of the present invention may further be used in combination with other pharmaceutically active agents such as those described herein. These agents include antidiabetic agents, lipid lowering agents, and blood pressure lowering agents such as statin drugs and the fibrates, and the like.

Methods are known in the art for determining effective doses for therapeutic and prophylactic purposes for the disclosed pharmaceutical compositions or the disclosed drug combinations, whether or not formulated in the same composition. For therapeutic purposes, the term "jointly effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term "jointly effective amount" refers to that amount of each active compound or pharmaceutical agent, alone or in combination, that treats or inhibits in a subject the onset or progression of a disorder as being sought by a researcher, veterinarian, medical doctor or other clinician. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both (or more) drugs are administered in an amount that is sub-therapeutic or sub-prophylactic if administered alone, but are therapeutic or prophylactic when administered together.

Anti-diabetic agents include thiazolidinedione and non-thiazolidinedione insulin sensitizers, which decrease peripheral insulin resistance by enhancing the effects of insulin at target organs and tissues.

Some of the following agents are known to bind and activate the nuclear receptor peroxisome proliferator-activated receptor-gamma (PPARγ) which increases transcription of specific insulin-responsive genes. Examples of PPAR-gamma agonists are thiazolidinediones such as:

(1) rosiglitazone (2,4-thiazolidinedione,5-((4-(2-(methyl-2-pyridinylamino) ethoxy) phenyl) methyl)-, (Z)-2-butenedioate (1:1) or 5-((4-(2-(methyl-2-pyridinylamino) ethoxy) phenyl) methyl)-2,4-thiazolidinedione, known as AVANDIA; also known as BRL 49653, BRL 49653C, BRL 49653c, SB 210232, or rosiglitazone maleate);

(2) pioglitazone (2,4-thiazolidinedione, 5-((4-(2-(5-ethyl-2-pyridinyl) ethoxy) phenyl) methyl)-, monohydrochloride, (+−)- or 5-((4-(2-(5-ethyl-2-pyridyl) ethoxy) phenyl) methy)-2,4-thiazolidinedione, known as ACTOS, ZACTOS, or GLUSTIN; also known as AD 4833, U 72107, U 72107A, U 72107E, pioglitazone hydrochloride (USAN));

(3) troglitazone (5-((4-((3,4-dihydro-6-hydroxy-2,5,7,8-tetramethyl-2H-1-benzopyran-2-yl)methoxy) phenyl) methyl)-2,4-thiazolidinedione, known as NOSCAL, REZULIN, ROMOZIN, or PRELAY; also known as CI 991, CS 045, GR 92132, GR 92132X);

(4) isaglitazone ((+)-5-[[6-[(2-fluorophenyl)methoxy]-2-naphthalenyl]methyl]-2,4-thiazolidinedione or 5-((6-((2-fluorophenyl)methoxy)-2-naphthalenyl) methyl-2,4-thiazolidinedione or 5-(6-(2-fluorobenzyloxy) naphthalen-2-ylmethyl) thiazolidine-2,4-dione, also known as MCC-555 or neoglitazone); and (5) 5-BTZD.

Additionally, the non-thiazolidinediones that act as insulin sensitizing agents include, but are not limited to:

(1) JT-501 (JTT 501, PNU-1827, PNU-716-MET-0096, or PNU 182716: isoxazolidine-3,5-dione, 4-((4-(2-phenyl-5-methyl)-1,3-oxazolyl) ethylphenyl-4) methyl-);

(2) KRP-297 (5-(2,4-dioxothiazolidin-5-ylmethyl)-2-methoxy-N-(4-(trifluoromethyl) benzyl) benzamide or 5-((2,4-dioxo-5-thiazolidinyl) methyl)-2-methoxy-N-((4-(trifluoromethyl) phenyl) m ethyl) benzamide); and (3) Farglitazar (L-tyrosine, N-(2-benzoylphenyl)-o-(2-(5-methyl-2-phenyl-4-oxazolyl) ethyl)- or N-(2-benzoylphenyl)-O-(2-(5-methyl-2-phenyl-4-oxazolyl) ethyl)-L-tyrosine, or GW2570 or GI-262570).

Other agents have also been shown to have PPAR modulator activity such as PPAR gamma, SPPAR gamma, and/or PPAR delta/gamma agonist activity. Examples are listed below:

(1) AD 5075;
(2) R 119702 ((+−)-5-(4-(5-Methoxy-1H-benzimidazol-2-ylmethoxy) benzyl) thiazolin-2,4-dione hydrochloride, or CI 1037 or CS 011);
(3) CLX-0940 (peroxisome proliferator-activated receptor alpha agonist/peroxisome proliferator-activated receptor gamma agonist);
(4) LR-90 (2,5,5-tris (4-chlorophenyl)-1,3-dioxane-2-carboxylic acid, PPARdelta/γ agonist);
(5) Tularik (PPARγ agonist);
(6) CLX-0921 (PPARγ agonist);
(7) CGP-52608 (PPAR agonist);
(8) GW-409890 (PPAR agonist);
(9) GW-7845 (PPAR agonist);
(10) L-764406 (PPAR agonist);
(11) LG-101280 (PPAR agonist);
(12) LM-4156 (PPAR agonist);
(13) Risarestat (CT-112);
(14) YM 440 (PPAR agonist);
(15) AR-H049020 (PPAR agonist);
(16) GW 0072 (4-(4-((2S,5S)-5-(2-(bis (phenylmethyl) amino)-2-oxoethyl)-2-heptyl-4-oxo-3-thiazo lidinyl) butyl) benzoic acid);
(17) GW 409544 (GW-544 or GW-409544);
(18) NN 2344 (DRF 2593);
(19) NN 622 (DRF 2725);
(20) AR-H039242 (AZ-242);
(21) GW 9820 (fibrate);
(22) GW 1929 (N-(2-benzoylphenyl)-O-(2-(methyl-2-pyridinylamino) ethyl)-L-tyrosine, known as GW 2331, PPAR alpha/γ agonist);
(23) SB 219994 ((S)-4-(2-(2-benzoxazolylmethylamino) ethoxy)-alpha-(2,2,2-trifluoroethoxy) benzen epropanoic acid or 3-(4-(2-(N-(2-benzoxazolyl)-N-methylamino) ethoxy) phenyl)-2 (S)-(2,2,2-trifluoroethoxy) propionic acid or benzenepropanoic acid, 4-(2-(2-benzoxazolylmethylamino) ethoxy)-alpha-(2,2,2-trifluoroethoxy)-, (alphaS)-, PPARalpha/γ agonist);
(24) L-796449 (PPAR alpha/γ agonist);
(25) Fenofibrate (Propanoic acid, 2-[4-(4-chlorobenzoyl) phenoxy]-2-methyl-, 1-methylethyl ester, known as TRICOR, LIPCOR, LIPANTIL, LIPIDIL MICRO PPAR alpha agonist);
(26) GW-9578 (PPAR alpha agonist);
(27) GW-2433 (PPAR alpha/γ agonist);
(28) GW-0207 (PPARγ agonist);
(29) LG-100641 (PPARγ agonist);
(30) LY-300512 (PPARγ agonist);
(31) NID525-209 (NID-525);
(32) VDO-52 (VDO-52);
(33) LG 100754 (peroxisome proliferator-activated receptor agonist);
(34) LY-510929 (peroxisome proliferator-activated receptor agonist);
(35) bexarotene (4-(1-(3,5,5,8,8-pentamethyl-5,6,7,8-tetrahydro-2-naphthalenyl) ethenyl) benzoic acid, known as TARGETIN, TARGRETYN, TARGREXIN; also known as LGD 1069, LG 100069, LG 1069, LDG 1069, LG 69, RO 264455); and
(36) GW-1536 (PPAR alpha/γ agonist).

(B) Other insulin sensitizing agents include, but are not limited to:

(1) INS-1 (D-chiro inositol or D-1,2,3,4,5,6-hexahydroxycyclohexane);
(2) protein tyrosine phosphatase 1 B (PTP-1B) inhibitors;
(3) glycogen synthase kinase-3 (GSK3) inhibitors;
(4) beta 3 adrenoceptor agonists such as ZD 2079 ((R)-N-(2-(4-(carboxymethyl) phenoxy) ethyl)-N-(2-hydroxy-2-phenethyl) ammonium chloride, also known as ICI D 2079) or AZ 40140;
(5) glycogen phosphorylase inhibitors;
(6) fructose-1,6-bisphosphatase inhibitors;
(7) chromic picolinate, vanadyl sulfate (vanadium oxysulfate);
(8) KP 102 (organo-vanadium compound);
(9) chromic polynicotinate;
(10) potassium channel agonist NN 414;
(11) YM 268 (5,5'-methylene-bis (1,4-phenylene) bismethylenebis (thiazolidine-2,4-dione);
(12) TS 971;
(13) T 174 ((+−)-5-(2,4-dioxothiazolidin-5-ylmethyl)-2-(2-naphthylmethyl) benzoxazole);
(14) SDZ PGU 693 ((+)-trans-2 (S-((4-chlorophenoxy) methyl)-7alpha-(3,4-dichlorophenyl) tetrahydropyrrolo (2,1-b) oxazol-5(6H)-one);
(15) S 15261 ((−)-4-(2-((9H-fluoren-9-ylacetyl) amino) ethyl) benzoic acid 2-((2-methoxy-2-(3-(trifluoromethyl) phenyl) ethyl) amino) ethyl ester);
(16) AZM 134 (Alizyme);
(17) ARIAD;
(18) R 102380;
(19) PNU 140975 (1-(hydrazinoiminomethyl) hydrazino) acetic acid;
(20) PNU 106817 (2-(hydrazinoiminomethyl) hydrazino) acetic acid;
(21) NC 2100 (5-((7-(phenylmethoxy)-3-quinolinyl) methyl)-2,4-thiazolidinedione;
(22) MXC 3255;
(23) MBX 102;
(24) ALT 4037;
(25) AM 454;
(26) JTP 20993 (2-(4-(2-(5-methyl-2-phenyl-4-oxazolyl) ethoxy) benzyl)-malonic acid dimethyl diester);
(27) Dexlipotam (5 (R)-(1,2-dithiolan-3-yl) pentanoic acid, also known as (R)-alpha lipoic acid or (R)-thioctic acid);
(28) BM 170744 (2,2-Dichloro-12-(p-chlorophenyl) dodecanoic acid);
(29) BM 152054 (5-(4-(2-(5-methyl-2-(2-thienyl) oxazol-4-yl) ethoxy) benzothien-7-ylmethyl) thiazolidine-2,4-dione);
(30) BM 131258 (5-(4-(2-(5-methyl-2-phenyloxazol-4-yl) ethoxy) benzothien-7-ylmethyl) thiazolidine-2,4-dione);
(31) CRE 16336 (EML 16336);
(32) HQL 975 (3-(4-(2-(5-methyl-2-phenyloxazol-4-yl) ethoxy) phenyl)-2(S)-(propylamino) propionic acid);
(33) DRF 2189 (5-((4-(2-(1-Indolyl) ethoxy) phenyl) methyl) thiazolidine-2,4-dione);
(34) DRF 554158;
(35) DRF-NPCC;
(36) CLX 0100, CLX 0101, CLX 0900, or CLX 0901;
(37) IkappaB Kinase (IKK B) Inhibitors

(38) mitogen-activated protein kinase (MAPK) inhibitors p38 MAPK Stimulators
(39) phosphatidyl-inositide triphosphate
(40) insulin recycling receptor inhibitors
(41) glucose transporter 4 modulators
(42) TNF-α antagonists
(43) plasma cell differentiation antigen-1 (PC-1) Antagonists
(44) adipocyte lipid-binding protein (ALBP/aP2) inhibitors
(45) phosphoglycans
(46) Galparan;
(47) Receptron;
(48) islet cell maturation factor;
(49) insulin potentiating factor (IPF or insulin potentiating factor-1);
(50) somatomedin C coupled with binding protein (also known as IGF-BP3, IGF-BP3, SomatoKine);
(51) Diab II (known as V-411) or Glucanin, produced by Biotech Holdings Ltd. or Volque Pharmaceutical;
(52) glucose-6 phosphatase inhibitors;
(53) fatty acid glucose transport protein;
(54) glucocorticoid receptor antagonists; and
(55) glutamine:fructose-6-phosphate amidotransferase (GFAT) modulators.

(C) Biguanides, which decrease liver glucose production and increases the uptake of glucose. Examples include metformin such as:
(1) 1,1-dimethylbiguanide (e.g., Metformin-DepoMed, Metformin-Biovail Corporation, or METFORMIN GR (metformin gastric retention polymer)); and
(2) metformin hydrochloride (N,N-dimethylimidodicarbonimidic diamide monohydrochloride, also known as LA 6023, BMS 207150, GLUCOPHAGE, or GLUCOPHAGE XR.

(D) Alpha-glucosidase inhibitors, which inhibit alpha-glucosidase Alpha-glucosidase converts fructose to glucose, thereby delaying the digestion of carbohydrates. The undigested carbohydrates are subsequently broken down in the gut, reducing the post-prandial glucose peak. Examples include, but are not limited to:
(1) acarbose (D-glucose, O-4,6-dideoxy-4-(((1S-(1alpha,4alpha,5beta,6alpha))-4,5,6-trihydroxy-3-(hydroxymethyl)-2-cyclohexen-1-yl) amino)-alpha-D-glucopyranosyl-(1-4)-O-alpha-D-glucopyranosyl-(1-4)-, also known as AG-5421, Bay-g-542, BAY-g-542, GLUCOBAY, PRECOSE, GLUCOR, PRANDASE, GLUMIDA, or ASCAROSE);
(2) Miglitol (3,4,5-piperidinetriol, 1-(2-hydroxyethyl)-2-(hydroxymethyl)-, (2R(2alpha,3beta,4alpha,5beta))- or (2R,3R,4R,5S)-1-(2-hydroxyethyl)-2-(hydroxymethyl-3,4,5-piperidinetriol, also known as BAY 1099, BAY M 1099, BAY-m-1099, BAYGLITOL, DIASTABOL, GLYSET, MIGLIBAY, MITOLBAY, PLUMAROL);
(3) CKD-711 (0-4-deoxy-4-((2,3-epoxy-3-hydroxymethyl-4,5,6-trihydroxycyclohexane-1-yl) amino)-alpha-b-glucopyranosyl-(1-4)-alpha-D-glucopyranosyl-(1-4)-D-glucopyranose);
(4) emiglitate (4-(2-((2R,3R,4R,5S)-3,4,5-trihydroxy-2-(hydroxymethyl)-1-piperidinyl) ethoxy) benzoic acid ethyl ester, also known as BAY o 1248 or MKC 542);
(5) MOR 14 (3,4,5-piperidinetriol, 2-(hydroxymethyl)-1-methyl-, (2R-(2alpha,3beta,4alpha,5beta))-, also known as N-methyldeoxynojirimycin or N-methylmoranoline); and
(6) Voglibose (3,4-dideoxy-4-((2-hydroxy-1-(hydroxymethyl) ethyl) amino)-2-C-(hydroxymethyl)-D-epi-inositol or D-epi-Inositol, 3,4-dideoxy-4-((2-hydroxy-1-(hydroxymethyl) ethyl) amino)-2-C-(hydroxymethyl)-, also known as A 71100, AO 128, BASEN, GLUSTAT, VOGLISTAT.

(E) Insulins include regular or short-acting, intermediate-acting, and long-acting insulins, non-injectable or inhaled insulin, tissue selective insulin, glucophosphokinin (D-chiroinositol), insulin analogues such as insulin molecules with minor differences in the natural amino acid sequence and small molecule mimics of insulin (insulin mimetics), and endosome modulators. Examples include, but are not limited to:
(1) Biota;
(2) LP 100;
(3) (SP-5-21)-oxobis (1-pyrrolidinecarbodithioato-S,S') vanadium,
(4) insulin aspart (human insulin (28B-L-aspartic acid) or B28-Asp-insulin, also known as insulin X14, INA-X14, NOVORAPID, NOVOMIX, or NOVOLOG);
(5) insulin detemir (Human 29B-(N6-(1-oxotetradecyl)-L-lysine)-(1A-21A), (1B-29B)-Insulin or NN 304);
(6) insulin lispro ("28B-L-lysine-29B-L-proline human insulin, or Lys(B28), Pro(829) human insulin analog, also known as lys-pro insulin, LY 275585, HUMALOG, HUMALOG MIX 75/25, or HUMALOG MIX 50/50);
(7) insulin glargine (human (A21-glycine, B31-arginine, B32-arginine) insulin HOE 901, also known as LANTUS, OPTISULIN);
(8) Insulin Zinc Suspension, extended (Ultralente), also known as HUMULIN U or ULTRALENTE;
(9) Insulin Zinc suspension (Lente), a 70% crystalline and 30% amorphous insulin suspension, also known as LENTE ILETIN II, HUMULIN L, or NOVOLIN L;
(10) HUMULIN 50/50 (50% isophane insulin and 50% insulin injection);
(11) HUMULIN 70/30 (70% isophane insulin NPH and 30% insulin injection), also known as NOVOLIN 70/30, NOVOLIN 70/30 PenFill, NOVOLIN 70/30 Prefilled;
(12) insulin isophane suspension such as NPH ILETIN II, NOVOLIN N, NOVOLIN N PenFill, NOVOLIN N Prefilled, HUMULIN N;
(13) regular insulin injection such as ILETIN II Regular, NOVOLIN R, VELOSULIN BR, NOVOLIN R PenFill, NOVOLIN R Prefilled, HUMULIN R, or Regular U-500 (Concentrated);
(14) ARIAD;
(15) LY 197535;
(16) L-783281; and
(17) TE-17411.

(F) Insulin secretion modulators such as:
(1) glucagon-like peptide-1 (GLP-1) and its mimetics;
(2) glucose-insulinotropic peptide (GIP) and its mimetics;
(3) exendin and its mimetics;
(4) dipeptyl protease (DPP or DPPIV) inhibitors such as
(4a) DPP-728 or LAF 237 (2-pyrrolidinecarbonitrile, 1-(((2-((5-cyano-2-pyridinyl) amino) ethyl) amino) acetyl), known as NVP-DPP-728, DPP-728A, LAF-237);
(4b) P 3298 or P32/98 (di-(3N-((2S,3S)-2-amino-3-methyl-pentanoyl)-1,3-thiazolidine) fumarate);
(4c) TSL 225 (tryptophyl-1,2,3,4-tetrahydroisoquinoline-3-carboxylic acid);
(4d) Valine pyrrolidide (valpyr);
(4e) 1-aminoalkylisoquinolinone-4-carboxylates and analogues thereof;
(4f) SDZ 272-070 (1-(L-Valyl) pyrrolidine);
(4g) TMC-2A, TMC-2B, or TMC-2C;

(4h) Dipeptide nitriles (2-cyanopyrrolodides);
(4i) CD26 inhibitors; and
(4j) SDZ 274-444;
(5) glucagon antagonists such as AY-279955; and
(6) amylin agonists which include, but are not limited to, pramlintide (AC-137, Symlin, tripro-amylin or pramlintide acetate).

The salts of the present invention may also increase insulin sensitivity with little or no increase in body weight than that found with the use of existing PPAR gamma agonists. Oral anti-diabetic agents may include insulin, sulfonylureas, biguanides, meglitinides, AGI's, PPAR alpha agonists, and PPAR gamma agonists, and dual PPAR alpha/gamma agonists.

The salts of the present invention also may increase fat and/or lipid metabolism, providing a method for losing weight, losing fat weight, lowering body mass index, lowering lipids (such as lowering triglycerides), or treating obesity or the condition of being overweight. Examples of lipid lowering agents include bile acid sequestrants, fibric acid derivatives, nicotinic acid, and HMGCoA reductase inhibitors. Specific examples include statins such as LIPITOR®, ZOCOR®, PRAVACHOL®, LESCOL®, and MEVACOR®, and pitavastatin (nisvastatin) (Nissan, Kowa Kogyo, Sankyo, Novartis) and extended release forms thereof, such as ADX-159 (extended release lovastatin), as well as Colestid, Locholest, Questran, Atromid, Lopid, and Tricor.

Examples of blood pressure lowering agents include antihypertensive agents, such as angiotensin-converting enzyme (ACE) inhibitors (Accupril, Altace, Captopril, Lotensin, Mavik, Monopril, Prinivil, Univasc, Vasotec, and Zestril), adrenergic blockers (such as Cardura, Dibenzyline, Hylorel, Hytrin, Minipress, and Minizide) alpha/beta adrenergic blockers (such as Coreg, Normodyne, and Trandate), calcium channel blockers (such as Adalat, Calan, Cardene, Cardizem, Covera-HS, Dilacor, DynaCirc, Isoptin, Nimotop, Norvace, Plendil, Procardia, Procardia XL, Sula, Tiazac, Vascor, and Verelan), diuretics, angiotensin II receptor antagonists (such as Atacand, Avapro, Cozaar, and Diovan), beta adrenergic blockers (such as Betapace, Blocadren, Brevibloc, Cartrol, Inderal, Kerlone, Lavatol, Lopressor, Sectral, Tenormin, Toprol-XL, and Zebeta), vasodilators (such as Deponit, Dilatrate, SR, Imdur, Ismo, Isordil, Isordil Titradose, Monoket, Nitro-Bid, Nitro-Dur, Nitrolingual Spray, Nitrostat, and Sorbitrate), and combinations thereof (such as Lexxel, Lotrel, Tarka, Teczem, Lotensin HCT, Prinzide, Uniretic, Vaseretic, Zestoretic).

Additionally, the salts of the present invention may further be administered in combination with a compound of formula (I) as disclosed in Maryanoff et al., U.S. Pat. No. 4,513,006, which is hereby incorporated by reference, in its entirety. A particularly preferred compound disclosed in Maryanoff et al., in U.S. Pat. No. 4,513,006 is topiramate, also known by its chemical name 2,3:4,5-di-O-isopropylidene-(β)-D-fructopyranose sulfamate, a compound of the following structure:

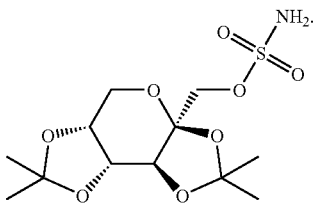

The compounds of formula (I) as disclosed in Maryanoff et al., U.S. Pat. No. 4,513,006 are useful in treating, preventing and/or preventing the progression of various disorders and diseases, including, but not limited to (a) epilepsy and related disorders; (b) diabetes, Syndrome X, impaired oral glucose tolerance and other metabolic disorders; (c) elevated blood pressure; (d) elevated lipid levels; (e) obesity and overweight condition, as would be recognized by one skilled in the art.

Preferably, one or more of the salts of the present invention are administered in combination with topiramate. Preferably, the topiramate is administered in an amount in the range of from about 10 to about 400 mg per day, more preferably from about 25 to about 250 mg per day, more preferably from about 25 to about 200 mg per day.

One skilled in the art will recognize that, both in vivo and in vitro trials using suitable, known and generally accepted cell and/or animal models are predictive of the ability of a test compound to treat or prevent a given disorder. One skilled in the art will further recognize that human clinical trails including first-in-human dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

EXAMPLE 1

{4-[2-Ethoxy-3-(4-trifluoromethyl-phenoxy)-propylsulfanyl]-2-methyl-phenoxy}-acetic acid L-Lysine di-hydrate salt

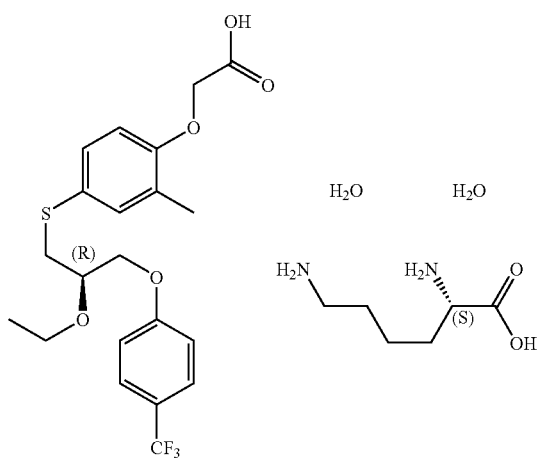

A 4 L Erlenmeyer flask equipped with a magnetic stir bar and nitrogen outlet was charged with {4-[2-ethoxy-3-(4-trifluoromethyl-phenoxy)-propylsulfanyl]-2-methyl-phenoxy}-acetic acid (502 g, 1.05 mol 93% purity) and methanol (2.3 L). The flask was warmed on a hot plate with stirring and then charged with L-Lysine (153.5 g, 1.05 mmol). The reaction mixture was diluted with water (112.5 mL, 6.25 mol). The reaction mixture was stirred and heated until the solids were dissolved. Upon reaching reflux the light yellow solution was hot filtered through a pad of Celite and the resulting light yellow solution was allowed to slowly cool to room temperature and then held at room temperature, with stirring for 3 days. The solid was isolated by vacuum filtration, the filter pad was rinsed with 1% (v/v) H₂O in methanol (~400 mL). The resulting solid was slurried in methanol (1 L) then filtered to yield the title compound as a white solid (lysine salt; di-hydrate).

m.p. 164° C.

¹H NMR δ (300 MHz, DMSO-d6) 7.64 (2H, d, J=8.8 Hz), 7.21-7.14 (2H, m), 7.12 (2H, d, J=8.8 Hz), 6.65 (1H, d, J=8.1 Hz), 4.23-4.08 (4H, m), 3.76-3.66 (1H, m), 3.54 (2H, dt, J=7.1 Hz, J=7.1 Hz), 3.27-3.19 (1H, m), 3.15-3.06 (2H, m), 2.73 (2H, dd, J=7.1 Hz, J=7.1 Hz), 2.12 (3H, s), 1.80-1.24 (6H, m), 1.07 (3H, t, J=7.1 Hz).

The corresponding non-hydrate, L-lysine salt was prepared by drying the di-hydrate, L-lysine salt in a drying oven, under vacuum.

EXAMPLE 2

{4-[2-Ethoxy-3-(4-trifluoromethylphenoxy)propyl-sulfanyl]-2-methylphenoxy}acetic acid, lysine salt, di-hydrate

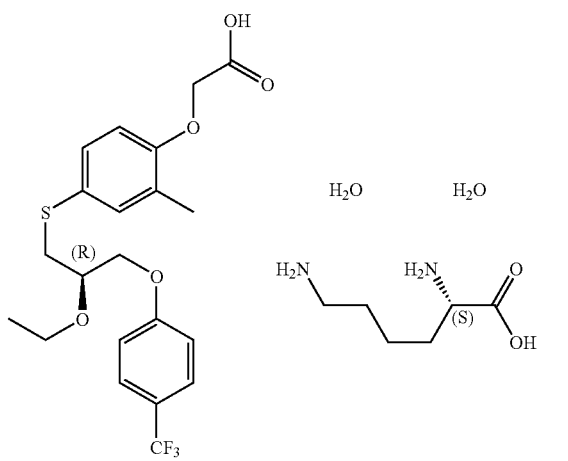

Two glass trays were charged with {4-[2-ethoxy-3-(4-trifluoromethylphenoxy)propylsulfanyl]-2-methylphenoxy}acetic acid, lysine salt (1.503 kg, 2.54 moles). A 3 L polypropylene beaker was charged with water (670 mL, 37.22 moles) and zinc sulfate heptahydrate (1 Kg, 3.48 moles), and the resulting solution was transferred to two empty glass trays. The trays were placed in the tray dryer in a sealed system. The solids were monitored until the appropriate amount of water was gained (5.5 to 6.5 wt %) to provide the di-hydrated material.

% KF=6.44 wt % (measured using a Metrohm 756 Coulometer)

EXAMPLE 3

{4-[2-Ethoxy-3-(4-trifluoromethyl-phenoxy)-propyl-sulfanyl]-2-methyl-phenoxy}-acetic acid L-Lysine non-hydrate salt

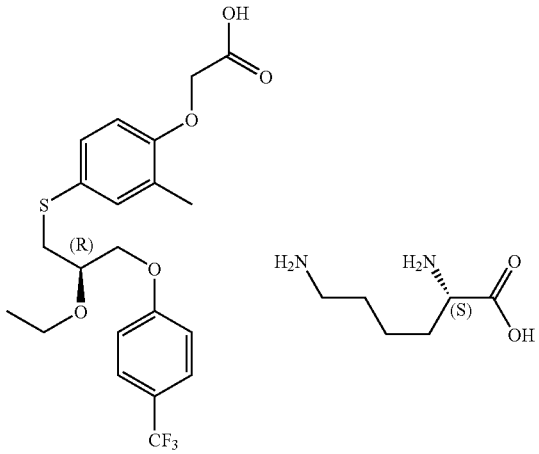

A 3-necked round bottom flask equipped with a thermometer, reflux condenser and a mechanical stirrer was charged with {4-[2-ethoxy-3-(4-trifluoromethyl-phenoxy)-propyl-sulfanyl]-2-methyl-phenoxy}-acetic acid (120 g, 0.235 mol 87% assay) and ethyl acetate (74.0 g). L-Lysine monohydrate (41.0 g, 0.250 mol) was dissolved in methanol (270.0 g), water (14.1 g) and added to the solution above. The reaction mixture was stirred and heated to reflux followed by a clear filtration. The light yellow solution was allowed to slowly cool to 20-25° C., with crystallization observed to start at about 35° C. The suspension was cooled to 0-5° C. and stirred for another 2 hours. The solid was isolated by vacuum filtration, and the filter pad was rinsed with cold methanol (54 g). The resulting white solid was dried at 60-70° C. under vacuum to yield the title compound.

EXAMPLE 4

{4-[2-Ethoxy-3-(4-trifluoromethylphenoxy)propyl-sulfanyl]-2-methylphenoxy}acetic acid, lysine salt, di-hydrate

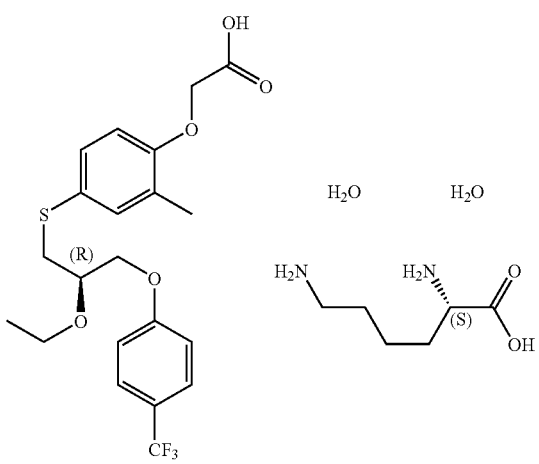

A vacuum oven was charged with {4-[2-ethoxy-3-(4-trifluoromethylphenoxy)propylsulfanyl]-2-methylphenoxy}acetic acid, lysine salt (115 g, 0.195 moles). A wet nitrogen stream was introduced at room temperature and 600-800 mbar pressure. The solids were monitored until the appropriate amount of water was gained (5.5 to 6.5 wt %) to yield the di-hydrated lysine salt, the title compound. Water content as a function of time was measured to be as listed in Table 6 below.

TABLE 6

| Water Content (%) | Time |
|---|---|
| 4.0% | 3 hr |
| 4.3% | 4 hr |
| 4.5% | 5 hr |
| 5.9% | 20 hr |

EXAMPLE 5

{4-[2-Ethoxy-3-(4-trifluoromethyl-phenoxy)-propylsulfanyl]-2-methyl-phenoxy}-acetic acid L-Lysine non-hydrate salt

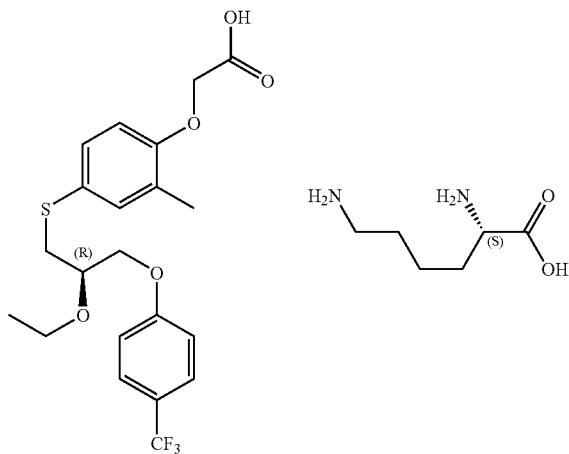

A 3-necked round bottom flask equipped with a thermometer, reflux condenser and a mechanical stirrer was charged with {4-[2-ethoxy-3-(4-trifluoromethyl-phenoxy)-propylsulfanyl]-2-methyl-phenoxy}-acetic acid (12.5 g, 0.0242 mol 86% assay) and technical ethanol (ethanol with water content: ≦6.5%; isopropanol content: ≦6.5%; and GLC purity ≧ 86 area %) (80.0 g). L-Lysine monohydrate (4.1 g, 0.250 mol) was dissolved in methanol (20.0 g) and added to the solution above. The reaction mixture was stirred and heated to reflux followed by a clear filtration. The light yellow solution was allowed to slowly cool to about 20-25° C., the crystallization starting at about 35° C. The suspension was cooled to about 0-5° C. and stirred for another 2 hours. The solid was isolated by vacuum filtration and the filter pad was rinsed with cold methanol (5.4 g). The resulting white solid was dried at about 60-70° C. under vacuum to yield the title compound.

EXAMPLE 6

As a specific embodiment of an oral composition, 100 mg of the di-hydrate, L-lysine salt prepared as in Example 1, is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A crystalline, L-lysine salt of (R)-{4-[2-Ethoxy-3-(4-trifluoromethyl-phenoxy)-propylsulfanyl]-2-methyl-phenoxy}-acetic acid, comprising the following X-ray diffraction peaks:

| Position [°2θ] | d-spacing [Å] |
|---|---|
| 5.270 | 16.7702 |
| 7.882 | 11.2170 |
| 9.683 | 9.1342 |
| 10.370 | 8.5312 |
| 11.611 | 7.6218 |
| 19.561 | 4.5383 |
| 19.921 | 4.4571 |
| 20.652 | 4.3009 |
| 21.963 | 4.0471 |
| 23.162 | 3.8403 |
| 23.710 | 3.7527 |
| 23.883 | 3.7228 |
| 23.969 | 3.7188. |

2. A crystalline, L-lysine salt of (R)-{4-[2-Ethoxy-3-(4-trifluoromethyl-phenoxy)-propylsulfanyl]-2-methyl-phenoxy}-acetic acid, comprising the following X-ray diffraction peaks:

| Position [°2θ] | d-spacing [Å] |
|---|---|
| 5.270 | 16.7702 |
| 9.683 | 9.1342 |
| 19.921 | 4.4571 |
| 23.162 | 3.8403. |

3. A crystalline, L-lysine salt of (R)-{4-[2-Ethoxy-3-(4-trifluoromethyl-phenoxy)-propylsulfanyl]-2-methyl-phenoxy}-acetic acid, comprising the following X-ray diffraction peaks:

| Position [°2θ] | d-spacing [Å] |
|---|---|
| 5.285 | 16.7225 |
| 9.255 | 9.5558 |
| 9.501 | 9.3085 |
| 9.976 | 8.8665 |
| 15.017 | 5.8997 |
| 18.417 | 4.8176 |
| 18.799 | 4.7205 |
| 19.102 | 4.6462 |
| 19.430 | 4.5686 |
| 19.990 | 4.4418 |
| 20.327 | 4.3689 |
| 20.643 | 4.3028 |
| 21.276 | 4.1762 |
| 21.989 | 4.0423 |
| 22.693 | 3.9185 |
| 23.187 | 3.8361 |
| 23.931 | 3.7186 |
| 24.084 | 3.6953 |
| 25.642 | 3.4741 |
| 26.462 | 3.3683 |
| 27.973 | 3.1897. |

4. A crystalline, L-lysine salt of (R)-{4-[2-Ethoxy-3-(4-trifluoromethyl-phenoxy)-propylsulfanyl]-2-methyl-phenoxy}-acetic acid, comprising the following X-ray diffraction peaks:

| Position [°2θ] | d-spacing [Å] |
|---|---|
| 9.255 | 9.5558 |
| 18.799 | 4.7205 |

-continued

| Position [°2θ] | d-spacing [Å] |
|---|---|
| 19.102 | 4.6462 |
| 20.643 | 4.3028 |
| 21.989 | 4.0423 |
| 23.187 | 3.8361. |

* * * * *